United States Patent [19]

Tanaka et al.

[11] Patent Number: 5,278,321
[45] Date of Patent: Jan. 11, 1994

[54] PROCESS FOR SIMULTANEOUSLY PRODUCING LACTONE AND AROMATIC CARBOXYLIC ACID

[75] Inventors: Toru Tanaka; Kazuo Tanaka, both of Kurashiki, Japan

[73] Assignee: Mitsubishi Gas Chemical Company, Inc., Tokyo, Japan

[21] Appl. No.: 927,964

[22] Filed: Aug. 11, 1992

[30] Foreign Application Priority Data

Aug. 13, 1991 [JP] Japan .................. 3-228463

[51] Int. Cl.⁵ .................. C07D 313/04; C07C 51/235
[52] U.S. Cl. .................. 549/272; 549/273; 549/295; 549/324; 549/328; 562/408; 562/412
[58] Field of Search ............... 549/272, 273, 295, 324, 549/328; 562/408, 412

[56] References Cited

U.S. PATENT DOCUMENTS 3,025,306  3/1962  Guest et al. .................. 260/343
3,483,222  12/1969  Sennewald et al. ............. 549/273

Primary Examiner—C. Warren Ivy
Assistant Examiner—Ba K. Trinh
Attorney, Agent, or Firm—Wenderoth, Lind & Ponack

[57] ABSTRACT

A process for simultaneously producing a lactone and an aromatic carboxylic acid, which comprises oxidizing a cyclic ketone and an aromatic aldehyde wherein: the cyclic ketone/aromatic aldehyde molar ratio is set at 1.1:1 to 20:1 and the throughput of the aromatic aldehyde per a unit reaction solution volume and a unit time is set at 0.05 to 1.5 mol/l.hour.

8 Claims, No Drawings

PROCESS FOR SIMULTANEOUSLY PRODUCING LACTONE AND AROMATIC CARBOXYLIC ACID

FIELD OF THE INVENTION

The present invention relates to a process for simultaneously producing a lactone and an aromatic carboxylic acid from a cyclic ketone and an aromatic aldehyde. Lactones are industrially useful as a solvent, an intermediate compound for synthesizing an organic compound and a raw material for a resin, and aromatic carboxylic acids are useful as a stabilizer for vinyl chloride.

PRIOR ART

It is known that a lactone and a carboxylic acid are produced from a cyclic ketone and an aldehyde. Japanese Patent Publication No. 39-5921 discloses a process for simultaneously producing an ε-caprolactone and a carboxylic acid, in which a cyclohexanone is allowed to react with an oxygen-containing gas and an aldehyde in the presence of a catalyst. JP,A 53-25516 discloses a process in which a cyclohexanone and an aldehyde are allowed to be co-present, a Cr compound is dissolved in the cyclohexanone and aldehyde, and the cyclohexanone and the aldehyde are co-oxidized with molecular oxygen. JP,B 55-36667 discloses a process for producing a lactone and a carboxylic acid, in which a cyclic ketone and an aldehyde are allowed to be co-present and co-oxidized in a liquid phase with molecular oxygen in the presence of a peracid.

The processes of Japanese Patent Publication No. 39-5921 and JP,A 53-25516, in which an aldehyde and a cyclohexanone are co-oxidized with molecular oxygen, are safe and advantageous in many ways. However, the selectivity to a lactone and the yields of a carboxylic acid are not satisfactory.

In the process of JP,B 55-36667 in which a cyclic ketone and an aldehyde are allowed to be co-present and co-oxidized with molecular oxygen in the presence of a peracid, the selectivity to a lactone is improved. Since, however, expensive peracid is used, this process involves a problem in view of safety and economy.

The present inventors focussed on aromatic peracids which are safer than aliphatic peracids, and made a study on a method of co-oxidizing a cyclic ketone and an aromatic aldehyde with molecular oxygen in the presence of an aromatic peracid. In this method, however, it has been found that the formation of aryl formate easily takes place and affects the yield of a lactone and the selectivity to an aromatic carboxylic acid as detailed below.

That is, in the reaction in which a cyclic ketone and an aromatic aldehyde are co-oxidized, a reaction to form a lactone and a reaction to form aryl formate take place at the same time, and the selectivity to an aromatic carboxylic acid decreases. Since the difference between the boiling point of aryl formate and the boiling point of a lactone is very small, it is very difficult to separate each from the other, and it is therefore difficult to obtain a high-quality product. In this co-oxidation method, it is required to inhibit the formation of aryl formate as much as possible.

SUMMARY OF THE INVENTION

It is an object of the present invention to provide a process for simultaneously producing a lactone and an aromatic carboxylic acid by a co-oxidation reaction of a cyclic ketone and an aromatic aldehyde, in which the formation of aryl formate is inhibited and the selectivity to each of the lactone and aromatic carboxylic acid is improved.

It is another object of the present invention to provide a process for simultaneously producing a lactone and an aromatic carboxylic acid, in which the quality of each product can be easily improved by improving the selectivity to each of the lactone and aromatic carboxylic acid and inhibiting the formation of aryl formate.

According to the present invention, there is provided a process for simultaneously producing a lactone of the formula (3),

wherein n is an integer of 2 to 11, and $R_0$ is a hydrogen atom, an alkyl group having 1 to 5 carbon atoms or a chlorine atom, and an aromatic carboxylic acid of the formula (4),

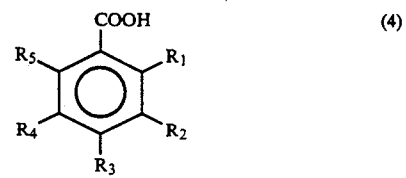

wherein each of $R_1$, $R_2$, $R_3$, $R_4$ and $R_5$ is independently a hydrogen atom, an alkyl group having 1 to 20 carbon atoms, a methoxy group, a hydroxy group, a phenyl group, a cyclohexyl group or a phenoxy group, which comprises oxidizing a cyclic ketone of the formula (1),

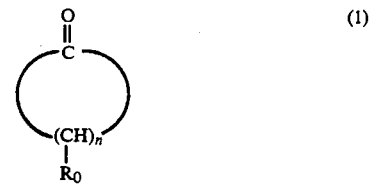

wherein n and $R_0$ are as defined above, and an aromatic aldehyde of the formula (2),

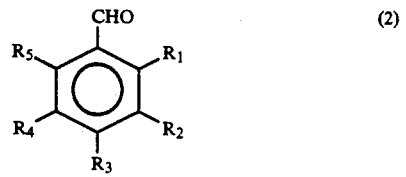

wherein $R_1$, $R_2$, $R_3$, $R_4$ and $R_5$ are as defined above, wherein: the cyclic ketone/aromatic aldehyde molar ratio is set at 1.1:1 to 20:1 and the throughput of the aromatic aldehyde per a unit reaction solution volume and a unit time is set at 0.05 to 1.5 mol/l.hour.

DETAILED DESCRIPTION OF THE INVENTION

The present inventors have made a diligent study on the method of co-oxidizing a cyclic ketone and an aromatic aldehyde, and have found the following: When the cyclic ketone/aromatic aldehyde molar ratio and the throughput of the aromatic aldehyde are set at the above-specified ranges, the amount of aryl formate as a byproduct is small, and a lactone and an aromatic carboxylic acid can be industrially advantageously produced with high selectivity to each of these products.

In the present invention, the above terms "throughput" and "selectivity" and the term "conversion" to appear later refer to the following.

Throughput (mol/hour.l): amount of raw material per unit amount (liter) of a reaction solution and unit time.

Selectivity (mol %): amount of a particular product based on the amount of raw material which has reacted.

Conversion (mol %): amount of raw material, which has reacted, based on fed raw material.

In the present invention, the cyclic ketone used as a raw material has the following formula,

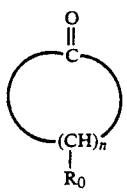
(1)

wherein n is an integer of 1 to 11, and $R_0$ is a hydrogen atom, an alkyl group having 1 to 5 carbon atoms or a chlorine atom.

Specific examples of the above cyclic ketone include cyclopropanone, cyclobutanone, cyclopentanone, cyclohexanone, cycloheptanone, cyclooctanone, cyclodecanone, 2-methylcyclohexanone, 3-methylcyclohexanone, 4-methylcyclohexanone, 2-ethylcyclohexanone and 2-chlorocyclohexanone.

In the present invention, the aromatic aldehyde used as the other raw material has the following formula (2),

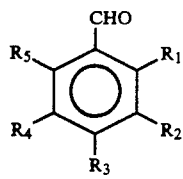
(2)

wherein each of $R_1$, $R_2$, $R_3$, $R_4$ and $R_5$ is independently a hydrogen atom, an alkyl group having 1 to 20 carbon atoms, a methoxy group, a hydroxy group, a phenyl group, a cyclohexyl group or a phenoxy group.

Specific examples of the above aromatic aldehyde include benzaldehyde, tolualdehyde, dimethylbenzaldehyde, trimethylbenzaldehyde, ethylbenzaldehyde, cominbenzaldehyde, butylbenzaldehyde, methoxybenzaldehyde, phenoxybenzaldehyde, hydroxybenzaldehyde, cyclohexylbenzaldehyde and biphenylaldehyde.

The lactone as a reaction product has the following formula (3),

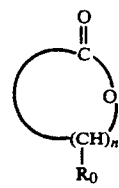
(3)

wherein n is an integer of 2 to 11, and $R_0$ is a hydrogen atom, an alkyl group having 1 to 5 carbon atoms or a chlorine atom.

The aromatic carboxylic acid as another reaction product has the following formula (4),

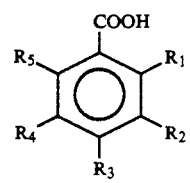
(4)

wherein each of $R_1$, $R_2$, $R_3$, $R_4$ and $R_5$ is independently a hydrogen atom, an alkyl group having 1 to 20 carbon atoms, a methoxy group, a hydroxy group, a phenyl group, a cyclohexyl group or a phenoxy group.

The reaction according to the present invention is represented by the following reaction scheme (5).

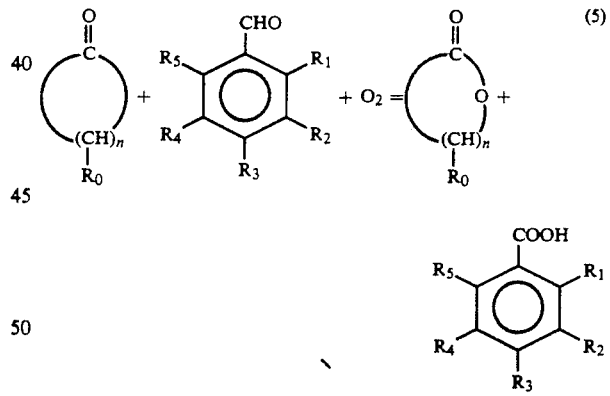
(5)

In the reaction between the cyclic ketone and the aromatic aldehyde in the above reaction scheme (5), aryl formate is easily formed according to the following reaction scheme (6).

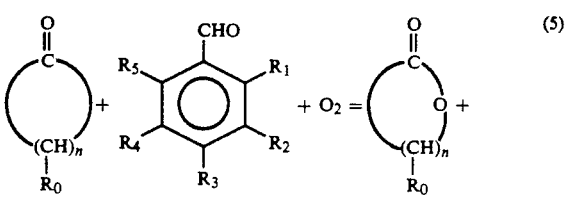
(5)

-continued

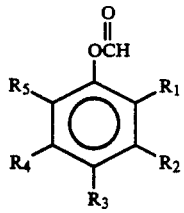

The above cooxidation reactions are assumed to proceed as follows. At first, the aromatic aldehyde is oxidized to form organic peracid, and the organic peracid and the cyclic ketone react with each other to form a lactone and an aromatic carboxylic acid. And, part of the organic peracid and part of the aromatic aldehyde react with each other to form aryl formate and an aromatic carboxylic acid. The reaction efficiency of the reaction scheme (5) according to the present invention is determined on the basis of the selectivity of the lactone based on the aromatic aldehyde which has reacted.

In the present invention, when the cyclic ketone and the aromatic aldehyde are fed to the reaction system, the cyclic ketone/aromatic aldehyde molar ratio is set at 1.1/1 to 10/1, preferably 4/1 to 10/1. With an increase in the feed ratio of the aromatic aldehyde, the amount of the aryl formate as a byproduct increases. The throughput of the aromatic aldehyde into the reaction system per a unit reaction solution volume and a unit reaction time is set at 0.05 to 1.5 mol/l.hour, preferably 0.15 to 0.8 mol/l.hour. When the throughput of the aromatic aldehyde is higher than the above upper limit, the amount of the aryl formate as a byproduct increases, and the selectivity to the aromatic carboxylic acid decreases. Further, the yield of the lactone decreases.

The cyclic ketone and the aromatic aldehyde are co-oxidized in the presence of molecular oxygen. The molecular oxygen includes pure oxygen, air, air of which the oxygen concentration is increased and a mixed gas containing oxygen and an inert gas (carbon dioxide or nitrogen). Air is generally used.

The reaction temperature is −20° to 150° C., preferably 10° to 120° C., more preferably 30° to 80° C. When the reaction temperature is too low, the reaction rate is low. When the reaction temperature is too high, the selectivity to each of the aromatic carboxylic acid and the lactone decreases.

The reaction pressure is generally atmospheric pressure to 60 kg/cm²G, preferably 20 to 50 kg/cm². With an increase in the reaction pressure, the reaction rate tends to increase an the yields increase. Further, the dissipation of the solvent out of the system can be prevented. It is therefore preferred to carry out the reaction under pressure. Since, however, no further effect can be obtained even if the reaction pressure exceeds 60 kg/cm²G, generally, the reaction is carried in the above pressure range.

The cooxidation reaction may be carried out in the absence of a catalyst. It is, however, preferred to use a metal catalyst such as cobalt, manganese, iron, platinum, palladium, vanadium, ruthenium, zirconium, aluminum, beryllium or copper. In particular, a cobalt catalyst is preferred, and is used in an amount of 0.1 to 50 ppm, preferably 0.5 to 10 ppm, on the basis of the total weight of the reaction solution. When the amount of the cobalt catalyst is less than 0.1 ppm, the reaction rate is small. When it exceeds 50 ppm, the selectivity to the aromatic peracid decreases.

In the present invention, the cooxidation reaction is generally carried out in the absence of a solvent. However, a solvent may be used as required. The solvent includes hydrocarbons such as hexane, cyclohexane and benzene, ketones such as acetone and methyl ethyl ketone, esters such as ethyl acetate and methyl benzoate, nitriles such as acetonitrile and benzonitrile, and lower organic carboxylic acids such as formic acid, acetic acid and propionic acid.

In the present invention, the reaction may be carried out by any one of a batch method, a semi-continuous method and a continuous method, and is preferably carried out by either a semi-continuous method or a continuous method.

According to the present invention, the formation of aryl formate as a byproduct, caused by aromatic aldehyde, is inhibited. Therefore, the selectivity to each of the lactone and the aromatic carboxylic acid is high, and the use efficiency of the aromatic aldehyde is therefore high.

Further, the present invention can spare expensive peracid. In the present invention, aromatic peracid is presumably formed from the aromatic aldehyde under a cooxidation reaction, and the selectivity to the lactone is presumably improved due to the so-formed aromatic peracid. The aromatic peracid is relatively stable, and the lactone and the aromatic carboxylic acid therefore can be produced industrially safely.

The lactone formed according to the present invention contains little impurities, and is thermally very stable.

The present invention will be further detailed by reference to Examples. However, the present invention shall not be limited to Examples. In Examples, "%" stands for "mol %" and "ppm" stands for "ppm by weight".

EXAMPLE 1

A 600-milliliter, SUS 316 autoclave having a stirrer and a reflux condenser was charged with 3.3 mg of $CoBr_2$ (hexahydrate) and 300 g of cyclohexanone, and while the mixture was maintained under a nitrogen pressure of 25 kg/cm²G at 35° C., the autoclave was continuously charged with 0.179 mol/hr (24 g/hr) of 2,4-dimethylbenzaldehyde and 1.02 mol/hr (100 g/hr) of cyclohexanone containing 11 ppm of $CoBr_2$ (hexahydrate). Further, air was introduced, and the oxygen concentration in a discharge gas was maintained at 10% by volume. In this case, the cyclohexanone/2,4-dimethylbenzaldehyde molar ratio was 5.7/1, and the throughput of 2,4-dimethylbenzaldehyde was 0.60 mol/l.hr.

After the reaction reached a stationary state, the resultant products were composition-analyzed to show that the conversion of 2,4-dimethylbenzaldehyde was 86 mol %, the selectivity to 2,4-dimethylbenzoic acid based on the 2,4-dimethylbenzaldehyde which had reacted was 98 mol % and the selectivity to xylenol formate was 0.5 mol % (and a trace amount of 2,4-xylenol was formed). Further, the conversion of cyclohexanone was 13.6 mol %, the selectivity to ε-caprolactone based on cyclohexanone which had reacted was 98 mol %, and the selectivity to ε-caprolactone based on the 2,4-dimethylbenzaldehyde which had reacted was 88 mol %.

EXAMPLE 2

Example 1 was repeated except that 2,4-dimethylbenzaldehyde was replaced with p-tolualdehyde. The resultant products were composition-analyzed to show that the conversion of p-tolualdehyde was 87 mol %, the selectivity to p-toluic acid based on the p-tolualdehyde which had reacted was 98 mol % and the selectivity to cresol formate was 0.3 mol % (and a trace amount of p-cresol was formed). Further, the conversion of cyclohexanone was 13.7 mol %, the selectivity to ε-caprolactone based on cyclohexanone which had reacted was 98 mol %, and the selectivity to ε-caprolactone based on the p-tolualdehyde which had reacted was 88 mol %.

EXAMPLE 3

Example 1 was repeated except that 2,4-dimethylbenzaldehyde was replaced with 2,4,5-trimethylbenzaldehyde. The resultant products were composition-analyzed to show that the conversion of 2,4,5-trimethylbenzaldehyde was 88 mol %, the selectivity to 2,4,5-trimethylbenzoic acid based on the 2,4,5-trimethylbenzaldehyde which had reacted was 97 mol % and the selectivity to trimethylphenol formate was 1.0 mol % (and a trace amount of trimethylphenol was formed). Further, the conversion of cyclohexanone was 13.4 mol %, the selectivity to ε-caprolactone based on cyclohexanone which had reacted was 97.1 mol %, and the selectivity to ε-caprolactone based on the 2,4,6-trimethylbenzaldehyde which had reacted was 84 mol %.

COMPARATIVE EXAMPLE 1

Example 1 was repeated except that the charging rate of 2,4-dimethylbenzaldehyde was changed to 0.537 mol/hr (72 g/hr) and that the charging rate of cyclohexanone containing 11 ppm of CoBr$_2$ (hexahydrate) was changed to 3.06 mol/hr (300 g/hr). In this case, the throughput of 2,4-dimethylbenzaldehyde was 1.79 mol/l.hr.

After the reaction reached a stationary state, the resultant products were composition-analyzed to show that the conversion of 2,4-dimethylbenzaldehyde was 71 mol %, the selectivity to 2,4-dimethylbenzoic acid based on the 2,4-dimethylbenzaldehyde which had reacted was 89 mol % and the selectivity to the total of xylenol formate and 2,4-xylenol was 7 mol %. Further, the conversion of cyclohexanone was 10.7 mol %, the selectivity to ε-caprolactone based on cyclohexanone which had reacted was 98 mol %, and the selectivity to ε-caprolactone based on the 2,4-dimethylbenzaldehyde which had reacted was 84 mol %.

COMPARATIVE EXAMPLE 2

Example 1 was repeated except that the charging rate of 2,4-dimethylbenzaldehyde was changed to 0.179 mol/hr (24 g/hr), that the charging rate of cyclohexanone was changed to 0.179 mol/hr (17.5 g/hr) and that 1.02 mol/hr (100 g/hr) of cyclohexanone containing 11 ppm of CoBr$_2$ (hexahydrate) was replaced with 38.5 g/hr of a solvent acetone containing 11 pm of CoBr$_2$ (hexahydrate). In this case, the 2,4-dimethylbenzaldehyde/cyclohexanone molar ratio was 1/1.

After the reaction reached a stationary state, the resultant products were composition-analyzed to show that the conversion of 2,4-dimethylbenzaldehyde was 93 mol %, the selectivity to 2,4-dimethylbenzoic acid based on the 2,4-dimethylbenzaldehyde which had reacted was 94 mol % and the selectivity to xylenol formate was 4 mol %. Further, the conversion of cyclohexanone was 69.8 mol %, and the selectivity to ε-caprolactone based on cyclohexanone which had reacted was 96 mol %.

In comparison of the results of Comparative Example 2 with the results of Example 1, the yields of 2,4-dimethylbenzoic acid and ε-caprolactone in Example 1 are low. However, the selectivity (1 mol %) to xylenol formate in Example 1 is much lower than the selectivity (4 mol %) in Comparative Example 2. Further, the selectivity to ε-caprolactone based on the 2,4-dimethylbenzaldehyde which reacted in Comparative Example 2 was 72%, while the selectivity to ε-caprolactone based on the 2,4-dimethylbenzaldehyde which reacted in Example 1 was 88%. This shows that an aromatic carboxylic acid and a lactone can be efficiently produced according to the present invention.

What is claimed is:

1. A process for simultaneously producing a lactone of the formula (3),

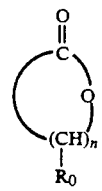

(3)

wherein n is an integer of 2 to 11, and R$_0$ is a hydrogen atom, an alkyl group having 1 to 5 carbon atoms or a chlorine atom, and an aromatic carboxylic acid of the formula (4),

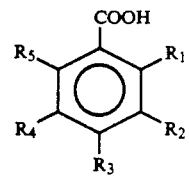

(4)

wherein each of R$_1$, R$_2$, R$_3$, R$_4$ and R$_5$ is independently a hydrogen atom, an alkyl group having 1 to 20 carbon atoms, a methoxy group, a hydroxy group, a phenyl group, a cyclohexyl group or a phenoxy group, which comprises oxidizing a cyclic ketone of the formula (1),

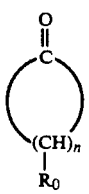

(1)

wherein n and R$_0$ are as defined above, and an aromatic aldehyde of the formula (2),

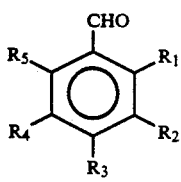

(2)

wherein $R_1$, $R_2$, $R_3$, $R_4$ and $R_5$ are as defined above, wherein: the cyclic ketone/aromatic aldehyde molar ratio is set at 4:1 to 20:1, the reaction pressure is 20 to 50 kg/cm$^2$.G and the throughput of the aromatic aldehyde per a unit reaction solution volume and a unit time is set at 0.05 to 1.5 mol/l.hour.

2. A process according to claim 1, wherein the cyclic ketone is cyclopropanone, cyclobutanone, cyclopentanone, cyclohexanone, cycloheptanone, cyclooctanone, cyclodecanone, 2-methylcyclohexanone, 3-methylcyclohexanone, 4-methylcyclohexanone, 2-ethylcyclohexanone or 2-chlorocyclohexanone.

3. A process according to claim 1, wherein the aromatic aldehyde is benzaldehyde, tolualdehyde, dimethylbenzaldehyde, trimethylbenzaldehyde, ethylbenzaldehyde, cumminbenzaldehyde, butylbenzaldehyde, methoxybenzaldehyde, phenoxybenzaldehyde, hydroxybenzaldehyde, cyclohexylbenzaldehyde or biphenylaldehyde.

4. A process according to claim 1, wherein the cyclic ketone/aromatic aldehyde molar ratio is set at 4/1 to 10/1.

5. A process according to claim 1, wherein the throughput of the aromatic aldehyde is set at 0.15 to 0.8 mol/l.hour.

6. A process according to claim 1, wherein the cyclic ketone and the aromatic aldehyde are oxidized with molecular oxygen at a temperature between $-20°$ C. and $150°$ C.

7. A process according to claim 1, wherein the cyclic ketone and the aromatic aldehyde are oxidized with molecular oxygen in the absence of a solvent.

8. A process according to claim 1, wherein the cyclic ketone and the aromatic aldehyde are oxidized in the presence of a cobalt catalyst in an amount of 0.1 to 50 ppm on the basis of the total weight of the reaction solution.

* * * * *